US011826189B2

(12) United States Patent
Van Rikxoort et al.

(10) Patent No.: US 11,826,189 B2
(45) Date of Patent: Nov. 28, 2023

(54) COMPUTER IMPLEMENTED METHOD FOR ESTIMATING LUNG PERFUSION FROM THORACIC COMPUTED TOMOGRAPHY IMAGES

(71) Applicant: Thirona B.V., Nijmegen (NL)

(72) Inventors: Eva Marjolein Van Rikxoort, Nijmegen (NL); Jean-Paul Charbonnier, Nijmegen (NL)

(73) Assignee: Thirona B.V., Nijmegen (NL)

( * ) Notice: Subject to any disclaimer, the term of this patent is extended or adjusted under 35 U.S.C. 154(b) by 470 days.

(21) Appl. No.: 17/004,073

(22) Filed: Aug. 27, 2020

(65) Prior Publication Data

US 2021/0059624 A1   Mar. 4, 2021

(30) Foreign Application Priority Data

Aug. 27, 2019 (NL) .................... 2023710

(51) Int. Cl.
| | |
|---|---|
| *A61B 6/00* | (2006.01) |
| *G16H 50/20* | (2018.01) |
| *G06N 20/00* | (2019.01) |
| *G06T 7/00* | (2017.01) |
| *A61B 6/03* | (2006.01) |

(52) U.S. Cl.
CPC ............ *A61B 6/507* (2013.01); *A61B 6/5217* (2013.01); *G06N 20/00* (2019.01); *G06T 7/0012* (2013.01); *G16H 50/20* (2018.01); *A61B 6/032* (2013.01); *G06T 2207/10081* (2013.01); *G06T 2207/10108* (2013.01); *G06T 2207/20081* (2013.01);

(Continued)

(58) Field of Classification Search
None
See application file for complete search history.

(56) References Cited

U.S. PATENT DOCUMENTS

| 2018/0260955 A1 | 9/2018 | Matsutani |
| 2019/0159744 A1 | 5/2019 | Mensah et al. |
| 2019/0220701 A1 | 7/2019 | Novak et al. |

OTHER PUBLICATIONS

Jang, Bum-Sup, et al. "Generation of virtual lung single-photon emission computed tomography/CT fusion images for functional avoidance radiotherapy planning using machine learning algorithms." Journal of medical imaging and radiation oncology 63.2 (2019): 229-235. (Year: 2019).*

(Continued)

*Primary Examiner* — Samah A Beg
(74) *Attorney, Agent, or Firm* — THE WEBB LAW FIRM

(57) ABSTRACT

The present invention relates to a computer implemented method for estimating lung perfusion from CT images, comprising the steps of: providing a CT image of at least a part of the lung, in particular a CT scan taken at inspiration, and more in particular a non-contrast CT scan taken at inspiration; providing the CT image to a trained computer implemented algorithm to estimate lung perfusion based on the CT image, wherein the trained computer implemented algorithm is trained by providing a set of CT images from at least a part of the lung, in particular a CT scan taken at inspiration, and more in particular a non-contrast CT scan taken at inspiration; providing perfusion information corresponding to the CT image; and training the computer implemented algorithm to learn to estimate perfusion in a CT image based on the reference perfusion information provided during training.

15 Claims, 3 Drawing Sheets

(52) U.S. Cl.
CPC ............... *G06T 2207/30061* (2013.01); *G06T 2207/30104* (2013.01)

(56) References Cited

OTHER PUBLICATIONS

Koster et al., "Approximated Perfusion from HRCT May Replace Nuclear Perfusion Imaging for Target Selection in Bronchoscopic Lung Volume Reduction Treatment", American Journal of Respiratory and Critical Care Medicine, 2019, A2634, vol. 199.
Matsuoka et al., "Relationship Between Quantitative CT of Pulmonary Small Vessels and Pulmonary Perfusion", AJR, 2014, pp. 719-724, vol. 202.
Ren et al., "Deriving Lung Perfusion Directly from CT Image Using Deep Convolutional Neural Network: A Preliminary Study", Springer Nature Switzerland AG 2019, pp. 102-109.

* cited by examiner

COMPUTER IMPLEMENTED METHOD FOR ESTIMATING LUNG PERFUSION FROM THORACIC COMPUTED TOMOGRAPHY IMAGES

CROSS-REFERENCE TO RELATED APPLICATION

This application claims priority to The Netherlands Patent Application No. 2023710 filed Aug. 27, 2019, the disclosure of which is hereby incorporated by reference in its entirety.

BACKGROUND OF THE INVENTION

Field of the Invention

The present invention relates to a computer implemented method for estimating lung perfusion from thoracic Computed Tomography (CT) images, more in particular from images that do not directly capture direct pulmonary perfusion information, and more in particular from (non)-contrast CT. The invention further relates to the training and use of a trained computer implemented method to estimate lung perfusion based on a CT image of at least one lung, in particular a CT image taken at inspiration and more in particular a non-contrast computer tomography image taken at inspiration.

Description of Related Art

One of the main organs in the human body are the lungs. The main function of the lungs is to regulate the oxygen and carbon dioxide levels in the systemic blood circulation of the body. For this purpose, the lungs can be divided into three structures: the airways, the pulmonary blood vessels, and the tissue in between called the lung parenchyma. The latter consists of alveolar sacs, i.e. the functional units where gas exchange between the vascular and bronchial system occurs, and connective tissue called the interstitium.

To image the lungs, CT is typically the imaging modality of choice, in particular in the diagnostics of respiratory diseases. It allows a fast and detailed evaluation of the aerated spaces, the supporting network of connective tissue (i.e. the interstitium), the airways, and the vessels. These structures play an important role in the functional effects of pulmonary diseases and therefore represent an important target for qualitative and quantitative assessment. CT is an imaging modality that is highly sensitive for capturing structural and anatomical information but does not capture direct information of pulmonary perfusion.

A thoracic CT scan shows the structural appearance at one time point and one specific inhalation state of the lungs. The attenuation of each location in a CT scan relates to the radiodensity of tissue within a voxel, as it reflects the localized absorption of X-rays. This attenuation is expressed in Hounsfield units (HU). A CT scanner may for instance be calibrated based on the radiodensity of water and the radiodensity of air, which are arbitrarily set to 0 HU and −1000 HU, respectively. The radiodensity of tissue on a CT image is expressed relative to these reference values and are visualized in gray-scale.

Because of the static nature of a thoracic CT, functional information about pulmonary blood perfusion is not directly available from the image. However, from the structural appearance of the lungs (e.g. pulmonary vasculature and lung parenchyma), an approximation of chronic perfusion defects can be estimated from a CT scan.

The objective of the present invention is to estimate perfusion and perfusion defects from a thoracic CT scan.

SUMMARY OF THE INVENTION

To this end, the present invention provides a computer implemented method for estimating lung perfusion from CT images, comprising the steps of: providing a CT image of at least a part of a lung, in particular a CT scan taken at inspiration, and more in particular a non-contrast CT scan taken at inspiration; providing the CT image to a trained computer implemented algorithm to estimate lung perfusion based on the CT image, wherein the trained computer implemented algorithm is trained by providing a set of CT images, from at least a part of the lung, in particular a set of CT scans taken at inspiration, and more in particular a set of non-contrast CT scans taken at inspiration; providing reference perfusion information, such as a perfusion image corresponding to the CT image, for instance provided by one or more image modalities like lung perfusion scintigraphy, Single Photon Computed Tomography (SPECT), dual-energy perfusion CT, contrast CT subtraction imaging, or perfusion based on multi temporal CT imaging; and training the computer implemented algorithm to estimate perfusion in the CT image based on the perfusion information or perfusion image corresponding to the CT image. Typically the training is performed by providing a set of multiple CT images and spatially matched reference perfusion images. In this context, the term CT image may be replaced with CT training image as well, such that the algorithm is trained by using training images with known perfusion information. Preferably the set of CT images is an independent set of CT images. Preferably the training of the algorithm is a one-time training phase.

BRIEF DESCRIPTION OF THE DRAWINGS

The invention will now be elucidated on the basis of non-limitative exemplary embodiments which are illustrated in the following figures. Corresponding elements are denoted in the figures by corresponding reference numbers. In the figures.

DESCRIPTION OF THE INVENTION

Figure 1:
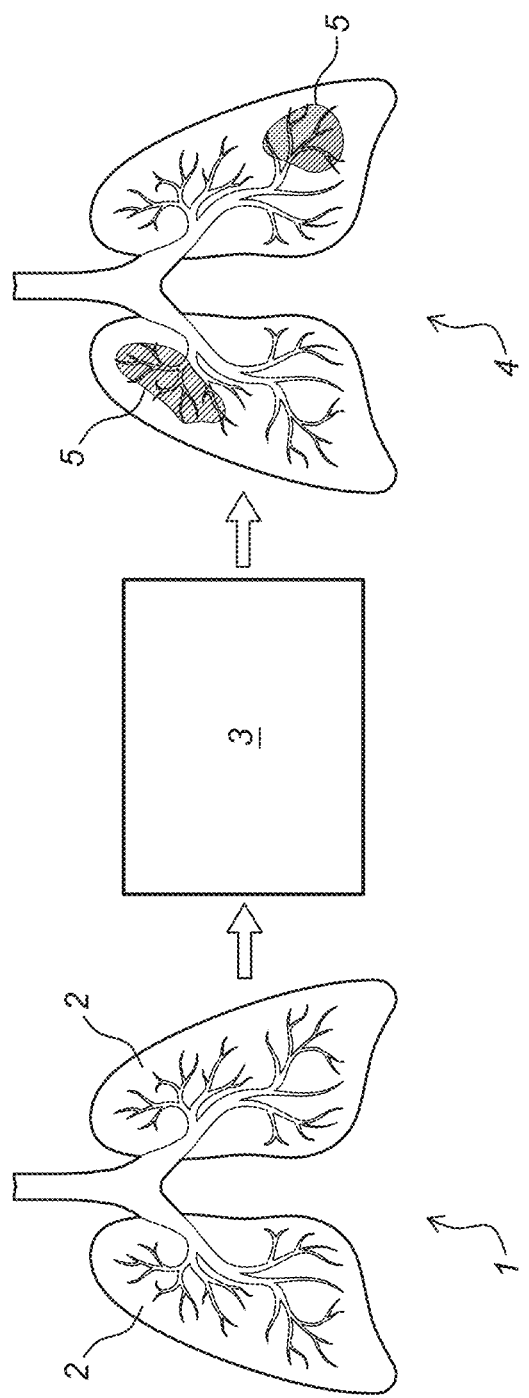
FIG. 1 schematically shows the method according to the invention.

FIG. 1 schematically shows the computer implemented method according to the present invention. On the left, a CT image (1) of the lungs (2) is provided. This image (1) is provided to a trained computer implemented algorithm (3). This algorithm (3) processes the image, and estimated perfusion based on the image (1). In FIG. 1, this perfusion is reflected in a heat map (4) which overlies the original image (1). As schematically indicated on the right side of FIG. 1, two hot spots (5) are shown, on the top left and on the bottom right.

Figure 2:
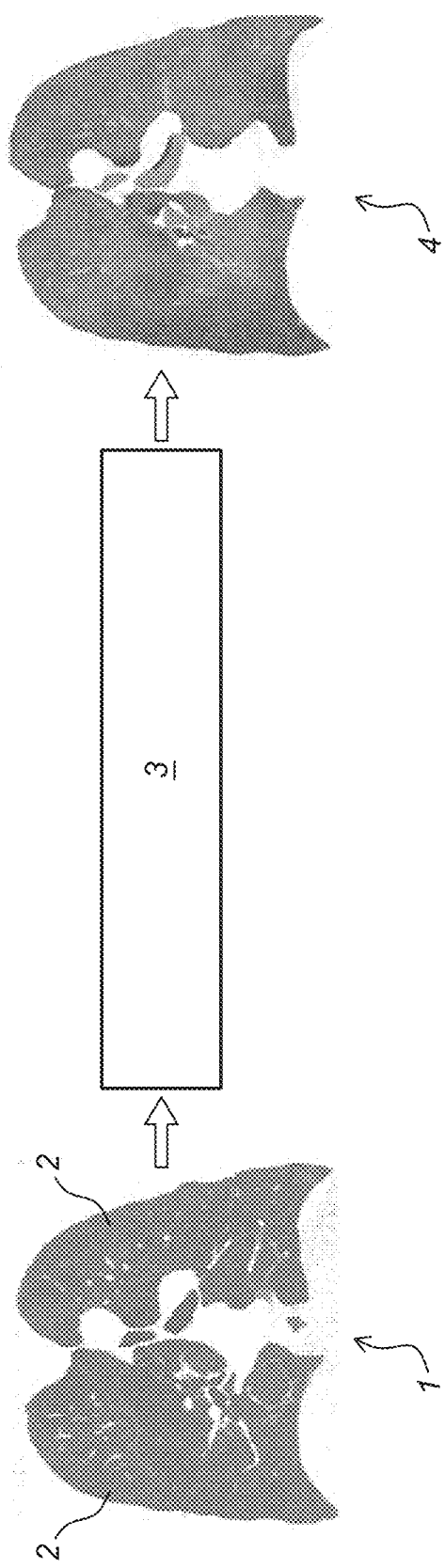
FIG. 2 shows the method of FIG. 1, showing schematic CT images.

FIG. 2 also shows the computer implemented method according to the present invention. Contrary to FIG. 1, FIG. 2 shows actual CT images of the lungs.

Figure 3:
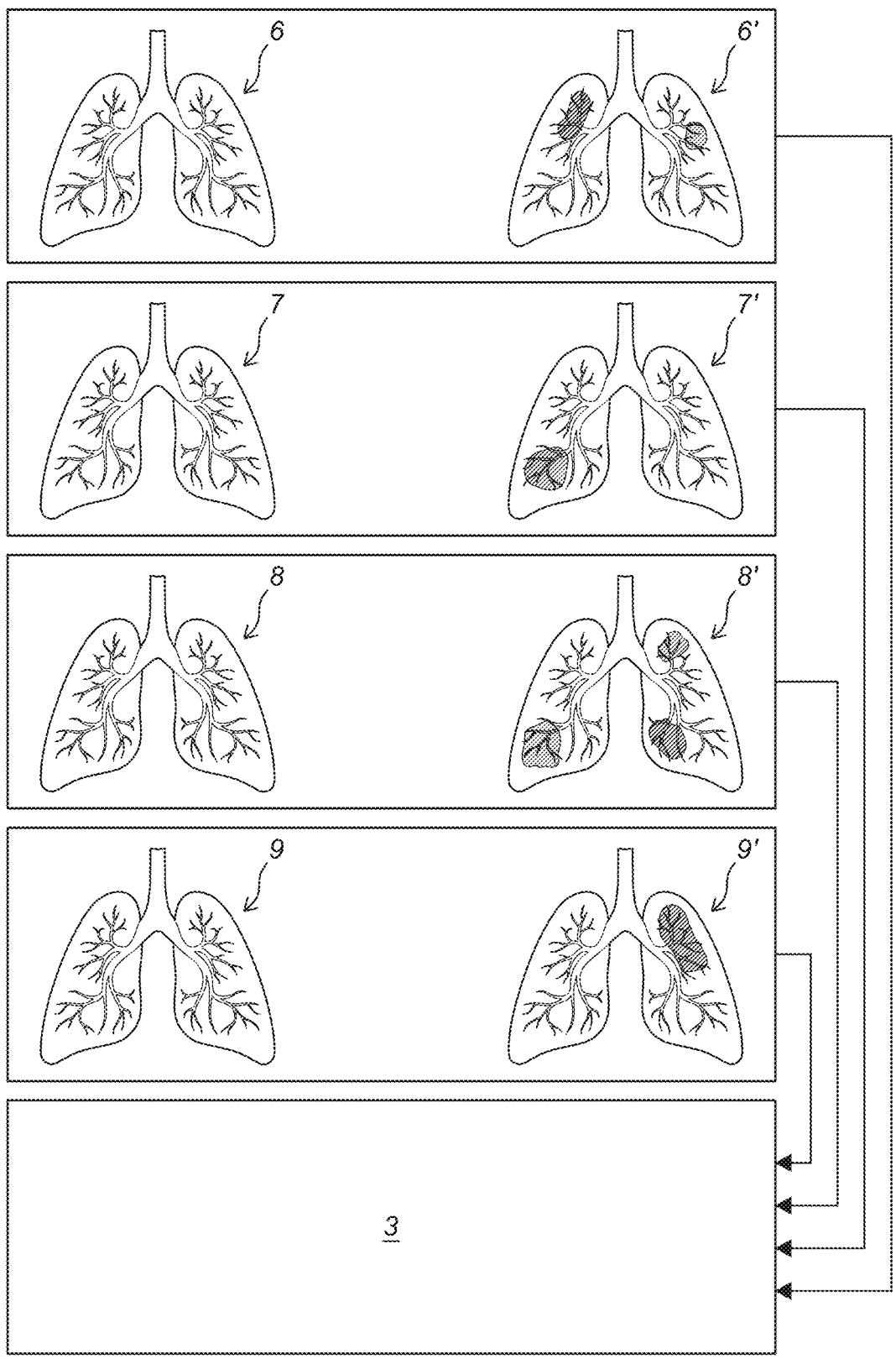
FIG. 3 schematically shows the training of the algorithm according to the present invention.

FIG. 3 schematically shows the, preferably one-time, training phase of the computer implemented algorithm (3) according to the invention. Sets of input CT images for training (6, 7, 8, 9) and perfusion information (6', 7', 8', 9') of the input images (6, 7, 8, 9) are provided to train the algorithm (3). The CT images and perfusion information can for instance be provided to the algorithm as a set, but can also be provided one at a time. After the algorithm has learned from the set of CT images and reference perfusion, the algorithm may be provided with a second set of validation data, now only with the CT images (although the perfusion information for this second set is also available). The output of the algorithm, which is the estimated perfusion based (solely) on the images of the second set, can then be checked against the known perfusion information of that set to verify the performance of the algorithm. If the algorithm is not fully trained yet, new training images can be provided to the algorithm to continue the training process until satisfactory results are achieved.

The method thus provides a trained computer implemented algorithm which, repeatably after being trained, is able to estimate perfusion based on relatively inexpensive CT scans, rather than requiring relatively expensive perfusion scans for each determination of perfusion.

The invention relies on a trained computer implemented algorithm that quantifies perfusion information (which is typically not readily available) from more easily accessible and relatively inexpensive scans, i.e. thoracic CT scans. The basic idea revolves around the assumption that perfusion related problems over time cause structural changes in the lungs, which can be detected rather well with conventional imaging like CT. During the development phase of the invention, the algorithm can be trained using a set of thoracic CT images for which at least some perfusion related information is available to serve as reference values for training. The algorithm learns to, for instance, relate structural changes in (CT) scans to areas of high perfusion or perfusion defects. After the one-time learning or training phase, the algorithm is able to analyse CT images without available perfusion information to estimate lung perfusion based on these CT images only. This eliminates the need to perform additional diagnostics (e.g. elaborate, difficult and expensive perfusion imaging) in order to obtain information on lung perfusion.

In use of the computer implemented method for estimating lung perfusion, no perfusion information is thus required. The only time this, relatively hard to obtain and expensive, information is required is during the training of the implemented algorithm. After training, only CT images or scans are required.

The, preferably one-time, training of the computer implemented algorithm may comprise the steps of providing a set of CT images (such as CT scans comprising at least one lung) from which the algorithm will learn to estimate lung perfusion. For each of the CT images provided, perfusion information is required. This information can be provided for instance by an imaging modality such as lung perfusion scintigraphy, Single Photon Computed Tomography (SPECT), dual-energy perfusion CT, contrast CT subtraction imaging, or perfusion based on multi temporal CT imaging. The algorithm is then trained, in particular since the algorithm is provided with the perfusion information, as well as the CT images, and the algorithm can learn to recognize or estimate perfusion based on features in the CT images.

Development of the computer implemented algorithm comprises of a series of steps. Depending on the available perfusion reference, either a perfusion image or another type of perfusion information corresponding to the CT image, these steps typically comprise of a) (spatially) matching perfusion information to the CT image, b) normalization of the perfusion values, and c) training the perfusion estimation algorithm. Once an algorithm is trained, only an input thoracic CT image is needed as input to the algorithm and none of these steps need to be repeated. The input lung image to the trained algorithm is for instance a high resolution non-contract CT scan taken at inspiration. The perfusion information can be provided in for instance the form of a SPECT scan. According to the invention, the terms image and scans relate to the same element.

Training of the computer implemented algorithm depends on the available reference perfusion information, either a perfusion image or perfusion information from another source corresponding to the CT image. When reference perfusion information is provided in the form of a 2D, 3D or 4D image, the CT image and the reference perfusion image should spatially match as closely as possible in order to train the algorithm appropriately.

Ideally, the perfusion information is provided in the form of a 3D image. When perfusion information is provided as a 3D image, the perfusion image and CT image should preferably have the same resolution. That way, specific information in the reference perfusion image can be spatially linked or matched to the CT image. The method may further comprise the steps of spatially matching the CT image and the reference perfusion information by transforming/modifying either the CT image and/or the perfusion scan, if needed, to improve the spatial relation between the structures in the CT scan to the perfusion information in the perfusion scan. Typically, the perfusion image is modified to closely match the input CT image.

The method development phase may comprise the step of transforming the input CT image or the reference perfusion image such that the perfusion information and the CT image have the same coordinate systems, and possibly the same resolution, which improves the correlation between the two. Transforming of the CT image and/or the perfusion image may be done with either a dedicated algorithm (such as image registration algorithms) or manually.

In step c) of development phase of the method, the computer implemented algorithm undergoes a one-time training procedure. Trained may be performed in a supervised manner, in particular using an end-to-end supervised deep learning architecture. There are several deep learning architectures that can be used to train the computer implemented algorithm to estimate perfusion according to the invention. As an example, use can be made of a 3D-Unet system, for instance one as described by Cicek et all (Özgün Çiçek, 2016). Such network has an analysis path and a synthesis part. In the analysis part of the network, layers one and two contain four 3×3×3 convolutions and layer three has three 3×3×3 convolutions. Each of the convolutions is followed by batch normalization, rectified linear unit (ReLu) and dropout layers. Each layer is followed by a 2×2×2 max pooling with strides of two in each dimension. In the synthesis path, first an up-convolution of size 2×2×2 is done and then, like in the analysis path, four 3×3×3 convolutions are applied each followed by batch normalization, rectified linear unit (ReLu) and dropout layers. Layers of equal resolution are connected in the analysis and synthesis paths. In the last layer a 1×1×1 convolution is done to have just one output channel. One channel output is enough to regress a value for each voxel in the input image. The input to the network is a cube of size 84×84×84 voxels with one channel. The output is also a cube of size 84×84×84 voxels. This way, the network has in total 2,679,153 trainable parameters.

Typical training parameters that can be applied in the algorithm according to the invention are listed in table 1.

TABLE 1

| Loss | Mean squared error |
|---|---|
| Optimizer | Adam |
| Learning rate | 0.0001 |
| Batch size | 2 |
| Stride size (training) | (24, 24, 24) |
| Stride size (validation) | (48, 48, 48) |

In the input step, data patches for training and validation are extracted from the entire image with a stride of size (24, 24, 24) and (48, 48, 48), respectively. Choosing a stride that is smaller than the size of the input data patch means that the input data patches overlap. Extracting input data patches from the entire image with a stride of size (24, 24, 24) during training means that each patch of size (24, 24, 24) from the input image is used multiple times during training and, more importantly, each time with different part of the image (the size of the input data patch to the network is (84, 84, 84)).

Supervised learning is one of the most common forms of machine learning. In supervised learning, a training set of examples is submitted as input to the algorithm during a one-time training phase. Each input is labelled with the desired output value (or reference value), and the system is thus trained to provide the desired outcome values based on each input value. The advantage of supervised deep learning is that the algorithm can be trained specifically for the task, based on the desired outcome. In supervised deep learning, the algorithm is trained end-to-end in a supervised way. During training, the algorithm is validated after every epoch, with a validation set of data that is not the used training set, to steer the training procedure and improve the algorithm further. Once the training procedure is done and the algorithm is optimized for the task at hand, only then new CT images are inputted into the algorithm for use.

The perfusion information, based on which the computer implemented method is trained, may be a perfusion image. The perfusion information is typically provided by an image modality like lung perfusion scintigraphy, Single Photon Computed Tomography (SPECT), dual-energy perfusion CT, contrast CT subtraction imaging, or perfusion based on multi temporal CT imaging. As output, these modalities often provide single perfusion values or 2D/3D/4D images with spatially located perfusion values.

Depending on the way the computer implemented algorithm is trained, the CT image to be studied may be standardized before the image is provided to the computer implemented algorithm. The standardization of the CT image for instance includes normalizing the values in the input image and/or clipping the information in the image such that the information lies between predetermined outer limits. These modifications may be used to improve the actions that can be taken to analyse the information. For instance, when the image is an inspiratory CT image, standardization can be done by clipping the voxel values such that everything below −1000 HU is clipped to −1000, and everything above 0 HU is clipped to 0. Next, this new range of voxel values can be normalized to values ranging from 0 to 1, 0 relating to −1000 HU and 1 relating to 0 HU. The radiodensity of tissue on a CT image is for instance expressed relative to these reference values and are visualized in gray scale. The modification may for instance comprise the step of changing the resolution of the CT image to match the resolution of a perfusion image during the training phase of the computer implemented algorithm. When for instance the resolution, or information density, of the perfusion information is lower than the resolution of the CT image, a single information value of perfusion information is not linked to a single information value of the CT image. To allow for a one-by-one comparison, or for instance a pixel-by-pixel or voxel-by-voxel comparison, the CT image and the perfusion information may first be adjusted to each other, which typically comprises downscaling the resolution of the CT image to match the resolution of the perfusion information.

The modification may comprise setting an upper and a lower threshold value for the CT image data, and adjusting the CT image data lower than the lower threshold value to the lower threshold value and adjusting the CT image data higher than the upper threshold value to the upper threshold value. By providing these thresholds, the CT image data always lies between the same values, which allows for a consistent application of the algorithm on multiple sources of data. The method may also comprise the step of normalizing the modified CT image data. By normalizing the image data, the values are distributed even more consistently.

A typical computer implemented algorithm according to the invention may comprise the training steps of providing a (modified) CT image, wherein for instance the resolution of the (modified) CT image does not spatially match the perfusion information; registering or transforming the reference perfusion image (or derivatives thereof) to the CT image, using that transformation to propagate the perfusion information onto the CT image to improve the spatial match; wherein the propagated perfusion image is provided to the computer implemented algorithm to serve as reference for training in step c).

The invention further relates to the use of a trained computer implemented method to estimate lung perfusion based on a CT image of at least one lung, in particular CT image taken at inspiration and more in particular a non-contrast CT image taken at inspiration. The trained computer implemented method may for instance be the computer implemented method according to the invention, wherein the features of the method may also be incorporated in the use thereof.

It will be apparent that the invention is not limited to the working examples shown and described herein, but that numerous variants are possible within the scope of the attached claims that will be obvious to a person skilled in the art.

The verb "comprise" and conjugations thereof used in this patent publication are understood to mean not only "comprise", but are also understood to mean the phrases "contain", "substantially consist of", "formed by" and conjugations thereof.

The invention claimed is:

1. A computer implemented method for estimating lung perfusion from thoracic computed tomography (CT) images, comprising the steps of:
 a. Receiving with at least one processor a CT image of at least a part of a lung; and
 b. Processing the CT image with a trained computer implemented algorithm executed on at least one processor to estimate lung perfusion based on the CT image;
 c. Wherein the trained computer implemented algorithm is trained by:
  i. Receiving with at least one processor a set of training CT images from at least a part of a lung;
  ii. Receiving with at least one processor reference perfusion information corresponding to the set of training CT images and normalizing the reference perfusion information; and iii. Processing the received set of training CT images and normalized reference perfusion information to train the computer implemented algorithm to estimate lung perfusion in a CT image based on the corresponding perfusion information.

2. The computer implemented method according to claim 1, wherein the training of the algorithm comprises the steps of comparing at least one training CT image of the set of training CT images and the perfusion information corresponding to the at least one training CT image, and modifying either the at least one training CT image of the set of training CT images and/or the perfusion information corresponding to the at least one training CT image to improve a spatial match or match a resolution of the images.

3. The computer implemented method according to claim 1, wherein in step c) the computer implemented algorithm is trained in a supervised manner.

4. The method of claim 3, wherein the supervised manner is a supervised deep learning manner.

5. The computer implemented method according to claim 1, wherein the perfusion information is a 2D perfusion image or a 3D perfusion image or a 4D perfusion image, or a combination of perfusion modalities.

6. The computer implemented method according to claim 1, wherein the received set of training CT images is modified, before the set of training CT images is processed to train the computer implemented algorithm.

7. The computer implemented method according to claim 6, wherein the modification comprises the step of changing the resolution of the set of training CT images or the reference perfusion information during the training of the computer implemented algorithm, to improve the spatial match.

8. The computer implemented method according to claim 6, wherein the modification comprises setting an upper and a lower threshold value for CT image data for the set of training CT images, and adjusting the CT image data lower than the lower threshold value to the lower threshold value and adjusting the CT image data higher than the upper threshold value to the upper threshold value.

9. The computer implemented method according to claim 6, comprising the step of normalizing the modified set of training CT images.

10. The computer implemented method according to claim 1, wherein the computer implemented algorithm is trained once, and the method is configured to be performed multiple times to estimate perfusion for multiple CT images.

11. The computer implemented method according to claim 1, wherein the training comprises the steps of:
Receiving with the at least one processor the set of training CT images;
Processing the set of training CT images to register the reference perfusion information corresponding to the set of training CT images, thereby transforming the set of training CT images; and
Using that transformation to propagate the reference perfusion information onto the set of training CT images, to improve a spatial match;
wherein the propagated reference perfusion information is provided to the computer implemented algorithm to serve as reference for training in step c).

12. The computer implemented method according to claim 1, wherein the CT image of at least the part of the lung is a non-contrast CT scan taken at inspiration.

13. The computer implemented method according to claim 1, wherein the reference perfusion information received by the at least one processor is a perfusion image corresponding to the set of training CT images provided by one or more image modalities.

14. The computer implemented method according to claim 13, wherein the one or more image modalities comprises lung perfusion scintigraphy, Single Photon Computed Tomography (SPECT), dual-energy perfusion CT, contrast CT subtraction imaging, or perfusion based on multi temporal CT imaging.

15. The computer implemented method according to claim 1, wherein the training of the computer implemented algorithm to estimate lung perfusion in the CT image is a one-time training.

* * * * *